(12) United States Patent
Johnson

(10) Patent No.: US 7,852,472 B1
(45) Date of Patent: Dec. 14, 2010

(54) SYSTEMS AND METHODS FOR SPECTROSCOPY USING OPPOSING LASER BEAMS

(76) Inventor: William M. Johnson, 103 Puritan La., Sudbury, MA (US) 01776

( * ) Notice: Subject to any disclaimer, the term of this patent is extended or adjusted under 35 U.S.C. 154(b) by 239 days.

(21) Appl. No.: 12/174,796

(22) Filed: Jul. 17, 2008

Related U.S. Application Data

(60) Provisional application No. 60/959,848, filed on Jul. 17, 2007.

(51) Int. Cl.
*G01J 3/30* (2006.01)
(52) U.S. Cl. ..................................................... 356/318
(58) Field of Classification Search ....................... None
See application file for complete search history.

(56) References Cited

U.S. PATENT DOCUMENTS 4,571,076 A  2/1986  Johnson

| | | | |
|---|---|---|---|
| 6,348,968 B2 * | 2/2002 | Autrey et al. | 356/432 |
| 6,577,929 B2 | 6/2003 | Johnson et al. | |
| 6,753,959 B2 * | 6/2004 | Hammer et al. | 356/330 |

* cited by examiner

*Primary Examiner*—Tu T Nguyen
(74) *Attorney, Agent, or Firm*—Weingarten, Schurgin, Gagnebin & Lebovici LLP

(57) ABSTRACT

A spectroscopy system uses a probe laser beam and an opposing excitation laser beam, i.e., running opposite to a direction of the probe laser beam, but transmitted co-linearly with one another along a same optical path. A thermal lens effect acting on the probe laser beam allows for controlling alignment of the two laser beams and allows for supplementary measurements of parameters for the spectroscopy system based on geometric analysis of detected image signals. The alignment of the two laser beams is controlled by detection of the probe laser beam with respect to the effects of the excitation laser beam on a medium through which the two laser beams are passing.

29 Claims, 8 Drawing Sheets

SYSTEMS AND METHODS FOR SPECTROSCOPY USING OPPOSING LASER BEAMS

RELATED APPLICATIONS

This application is a non-provisional application of U.S. Ser. No. 60/959,848, entitled "Dual Opposed Beam Thermal Lens Spectroscopy (DOBTLS)," filed Jul. 17, 2007, the entire contents of which is hereby incorporated by reference for all purposes.

FIELD OF THE INVENTION

The present invention relates to spectroscopy, e.g., thermal lens spectroscopy, and improvements to the measurement, alignment and accuracy of spectroscopic measurements.

BACKGROUND OF THE INVENTION

As is known, spectroscopic analysis is used in a significant number of industries as a technique to determine an amount of material in, for example, a solution or gas. More particularly, analytic instruments that implement spectroscopy or spectrometry are used in physical and analytical chemistry in order to identify unknown substances.

There are many different spectroscopy systems in use. One type of optical beam spectroscopy is photothermal (thermal) spectroscopy that is used to measure the optical absorption and thermal characteristics of a sample. A thermal state of a sample is changed due to the absorption of radiation, usually due to effects of a laser beam directed through the sample. Any light that is absorbed by the sample, and not lost by transmission, results in heating of the sample. Changes in temperature, pressure, and density that may occur can be used to determine photothermal spectroscopic measurements. Photothermal lens spectroscopy (PTS or TLS) measures the thermal blooming that occurs when a beam of light heats a transparent sample. Often, this type of spectroscopy is applied to measure the small amounts of substances that may be found in a gas or liquid solution.

A second type of spectroscopy, Cavity Ring-down Spectroscopy (CRDS) measures the optical absorption of excitation energy over time. A CRDS system also measures very small amounts of substances that may be in a gas or liquid solution.

Currently, the analytical spectroscopy instrumentation market is more than $20 billion (USD) annually. The analytical technologies that include liquid chromatography, mass spectrometry, and thermal analysis account for about 25% of this total. Advances are being sought in order to attain new levels as to miniaturization of the equipment, increased resolution, increased sensitivity, and increased speed for liquid chromatography analysis. These increases will have dramatic impacts on laboratory productivity. Further, a portable and fast analysis instrument will create new application areas that cannot be serviced by larger and slower laboratory instruments.

Accordingly, what is needed is an improvement to spectroscopy instrumentation in order to increase ease of portability, speed of analysis, sensitivity of analysis with increased resolution and the detection of minute quantities.

SUMMARY OF THE INVENTION

There is provided, in accordance with an embodiment of the present invention, an apparatus for spectrometry, comprising: a first laser source adapted to emit an excitation laser beam in a first direction along a first optical path and into a medium; a second laser source adapted to emit a probe laser beam in a second direction along the first optical path and through the medium, the second direction opposite the first direction; a detector oriented to detect the probe laser beam after passing through the medium; and a controller, coupled to the detector, adapted to maintain co-linearity of the excitation laser beam and the probe laser beam as a function of the detected probe laser beam.

In another embodiment, a method of controlling accuracy of first and second laser beams in a spectrometry system comprises: generating a first laser beam in a first direction along a first optical path through a medium; generating a second laser beam in a second direction, opposite the first direction, along the first optical path and through the medium; detecting energy of the second laser beam after passing through the medium; and maintaining co-linearity of the first and second laser beams with one another as a function of the detected energy.

Further, a method of maintaining co-linearity of first and second laser beams, wherein the second laser beam defines an optical path along which the first laser beam is to be aligned, comprises: generating the first laser beam in a first direction along the optical path through a medium; generating the second laser beam in a second direction, opposite the first direction, along the optical path and through the medium; detecting energy of the second laser beam after passing through the medium; and maintaining the co-linearity of the first and second laser beams with one another as a function of the detected energy, wherein the first laser beam has a higher energy than the second laser beam.

A method of characterizing a medium, in accordance with one embodiment, comprises: generating a first laser beam in a first direction along an optical path through the medium; generating a second laser beam in a second direction, opposite the first direction, along the optical path and through the medium; detecting energy of the second laser beam after passing through the medium; and determining one or more characteristics of the medium as a function of the detected energy.

BRIEF DESCRIPTION OF THE DRAWINGS

The above and further advantages of the present invention may be better understood by referring to the following description in conjunction with the accompanying drawings in which.

Figure 1:
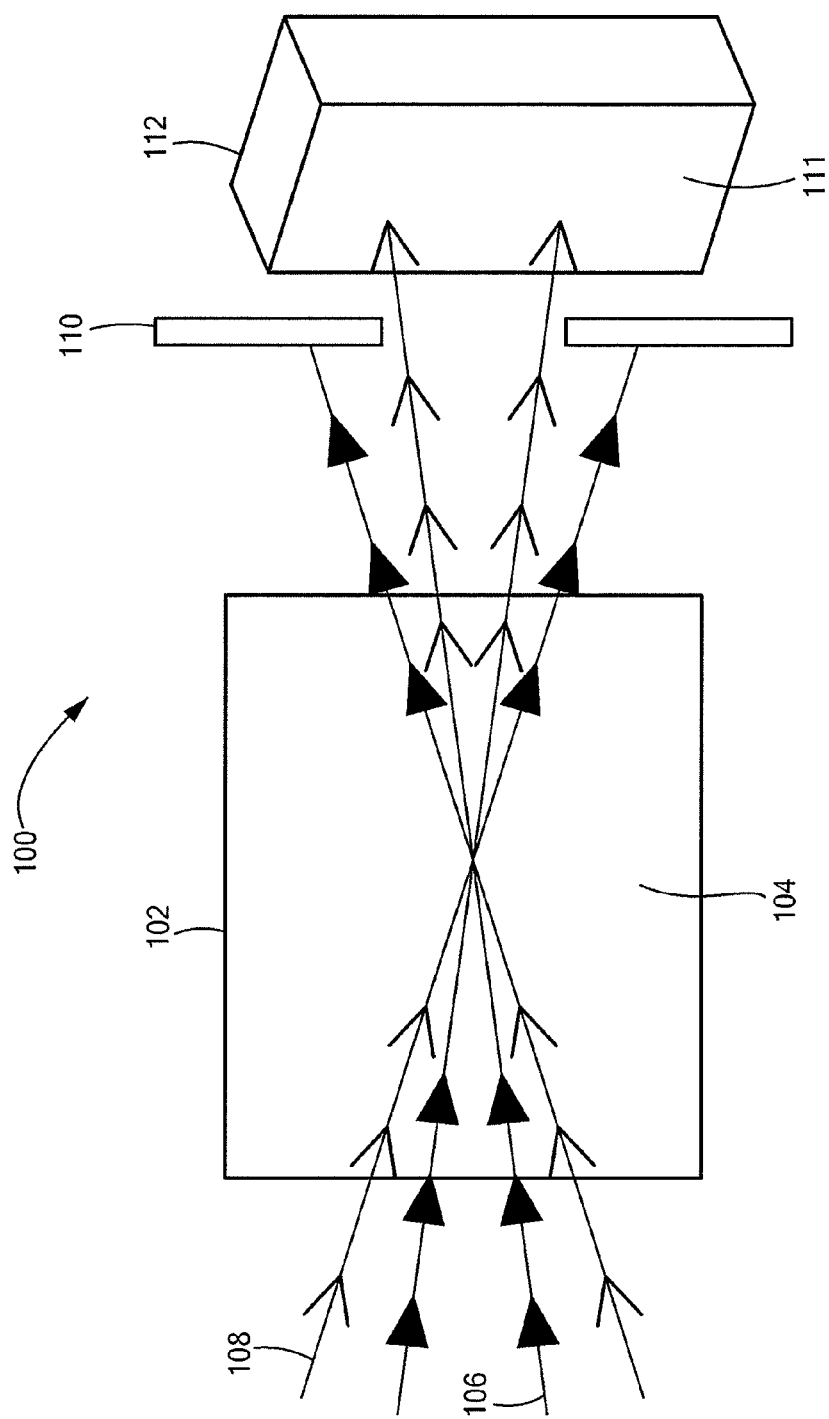
FIG. 1 is a diagram of a known thermal lens spectroscopy system.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

Embodiments of the present invention are directed to systems and methods for providing increased accuracy of spectroscopic systems by including improved alignment characteristics leading to a better signal-to-noise ratio, increased speed, increased resolution and increased sensitivity. According to one or more embodiments of the present invention, two opposed laser beams are directed through a medium, e.g., a sample solution, and aligned with one another. Advantageously, the increased alignment allows for the spectroscopic measurement to be made more accurately. Additionally, the opposed beams provide an additional mechanism for characterizing or measuring an unknown medium or sample.

In the following detailed description, numerous specific details are set forth in order to provide a thorough understanding of embodiments of the present invention. It will be understood by those of ordinary skill in the art that embodiments of the present invention may be practiced without some of these specific details. In other instances, well-known methods, procedures, components and structures may not have been described in detail so as not to obscure the present invention.

Prior to explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Further, it should be noted that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The entire contents of U.S. non-provisional application Ser. No. 60/959,848, entitled "Dual Opposed Beam Thermal Lens Spectroscopy (DOBTLS)," filed Jul. 17, 2007, are incorporated by reference herein for all purposes.

Referring now to FIG. 1, a known thermal lens spectroscopy system 100 includes a container 102 in which an unknown medium or sample solution 104 is placed. An excitation laser beam 106 is directed through the sample solution 104 within the container 102. A probe laser beam 108 is also directed through the sample solution 104 and the container 102, intended to be along a same optical path and in a same direction as the excitation laser beam 106. A filter 110 is provided to block the excitation laser beam 106 from passing through and impinging on a detecting surface 111 of a diode detector 112. Generally, the filter 110 is not a selective filter, i.e., one that selectively filters out the excitation laser beam 106 and, therefore, part of the excitation laser beam 106 does get through to the diode detector 112. As a result, some amount of excitation laser beam 106 energy, and the probe laser beam 108 energy, after having passed through the sample solution 104, impinges on the diode detector 112.

The diode detector 112 merely detects an amplitude of the energy that falls upon its detecting surface. The measured amplitude is a function of the heating of the sample solution 104 by the excitation laser beam 106. The change of the amplitude of the received probe laser beam 108 energy is analogous to amplitude modulation detection. Amplitude noise will have an effect on the amplitude measurement accuracy.

The filter 110 partially blocks the excitation laser beam 106 from impinging on the diode detector 112. As a result of this partial blocking, i.e., the imperfect function of the filter 110, there is a reduction in the signal-to-noise ratio because part of the detected energy falling on the diode detector 112 is due, to some amount, to the excitation laser beam 106 as the filter 110 has not blocked all of the excitation laser beam 106 energy. Thus, the signal is noisy as it includes residual noise energy from the excitation laser beam 106.

As is known, the probe laser beam 108 and the excitation laser beam 106 should be aligned in order to provide a maximum probe laser beam intensity response due to the sample being heated by the excitation laser beam 106. As the laser beams are intended to be co-linear to one another and directed in the same direction, an alignment problem arises and a signal detection problem requiring the filter 110 to eliminate the excitation beam energy on the detector is necessary. This setup causes a detection problem because the high power excitation laser beam 106 requires filtering so that its energy does not mask the signal from the relatively lower power probe laser beam 108 on the diode detector 112. To further complicate the issue, as the sample solution 104 absorbs differing amounts of the excitation energy from the excitation laser beam 106, the detected probe laser beam 108 intensity will change.

Figure 2:
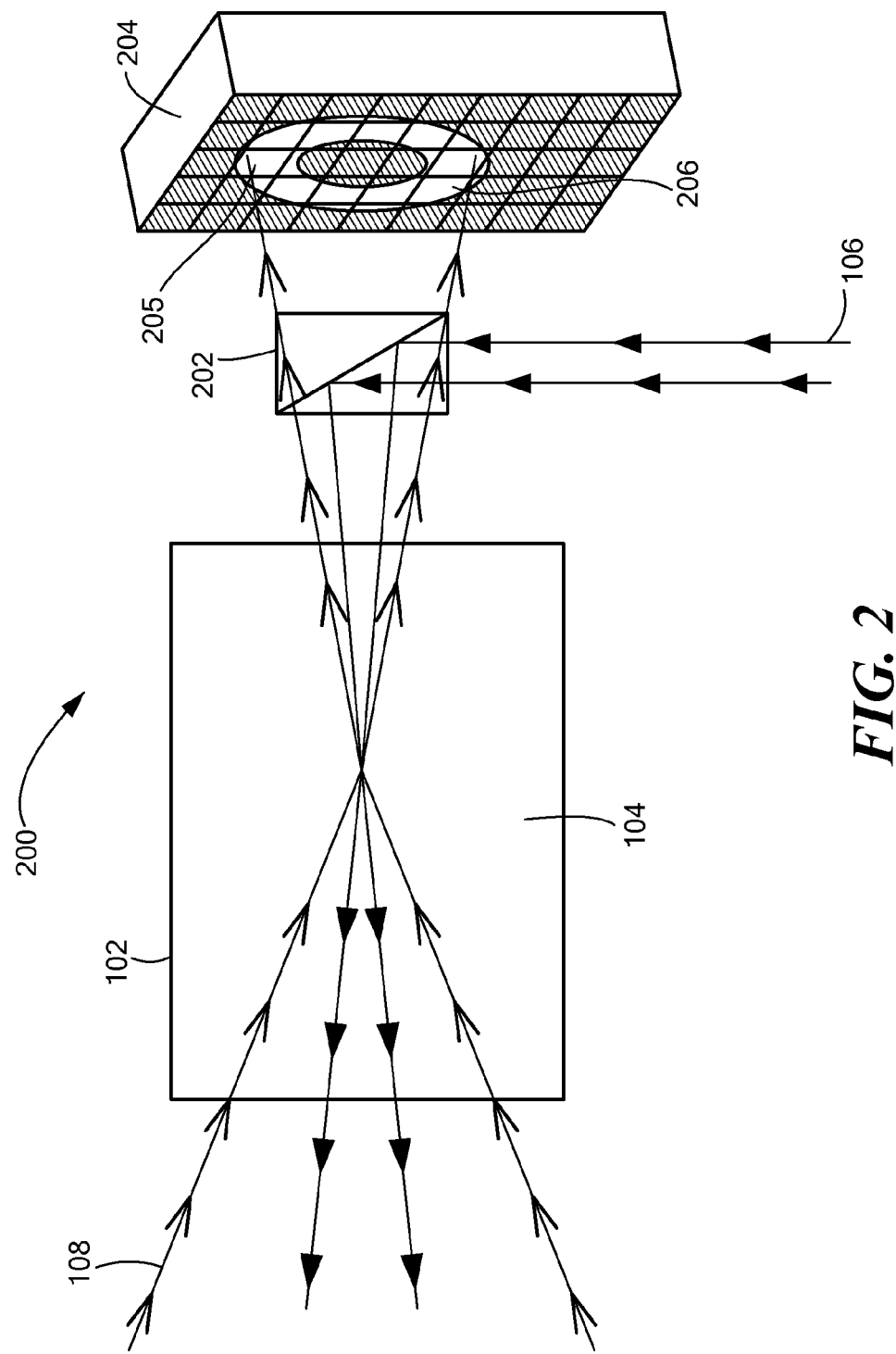
FIG. 2 is a diagram of a thermal lens spectroscopy system in accordance with one embodiment of the present invention.

Referring now to FIG. 2, one embodiment of the present invention is a thermal lens spectroscopy system 200 that incorporates an excitation laser beam 106 and a probe laser beam 108 that are directed in opposite directions relative to one another along a same optical path. The excitation laser beam 106 is directed through a beam splitter 202 and passes through the sample solution 104 within the container 102 along the optical path in a first direction. One of ordinary skill in the art will appreciate that other configurations of providing the laser beam 106 are possible. The probe laser beam 108 is directed along the same optical path as the excitation laser beam 106, however, the probe laser beam 108 is directed in a direction opposite to that of the excitation laser beam 106. The probe laser beam 108 also passes through the sample solution 104 and through the beam splitter 202 and then impinges upon a surface of a mosaic or matrix array detector 204 comprising a plurality of detector elements 205. The mosaic array detector 204, in one embodiment, comprises a plurality of energy detectors 205, for example, a CCD device, an array of photo diodes, or any equivalent device as known to one of ordinary skill in the art. There are various types of mosaic detectors available to detect the energy. In one embodiment of the present invention, an Electron Bombarded CMOS (EBCMOS) array is used because of its high sensitivity, on the order of single photon detection and its flexible CMOS operation.

As is known in the art of thermal lens spectroscopy, the excitation laser beam 106 has a greater power or energy level, generally, than that of the probe laser beam 108. Accordingly, as the excitation laser beam 106 travels along the optical path, the excitation laser beam 106 heats the sample solution 104 producing a density gradient there along that has a lower density than a surrounding portion of the sample solution 104. When the excitation laser beam 106 and the probe laser beam 108 are substantially co-linear along the optical path, the probe laser beam 108 is traveling through a lower density portion of the sample solution 104. Generally, the sample solution 104 is a fluid where the fluid can be a gas or a liquid and where the liquid can include water. The creation of this lower density area/volume along the path of the excitation laser beam 106, as known to those of ordinary skill in the art, is referred to as either a thermal lens, a negative lens, or a blooming collimator as explained, generally, in U.S. Pat. No. 4,571,076, which is incorporated by reference herein for all purposes.

Figure 3A:
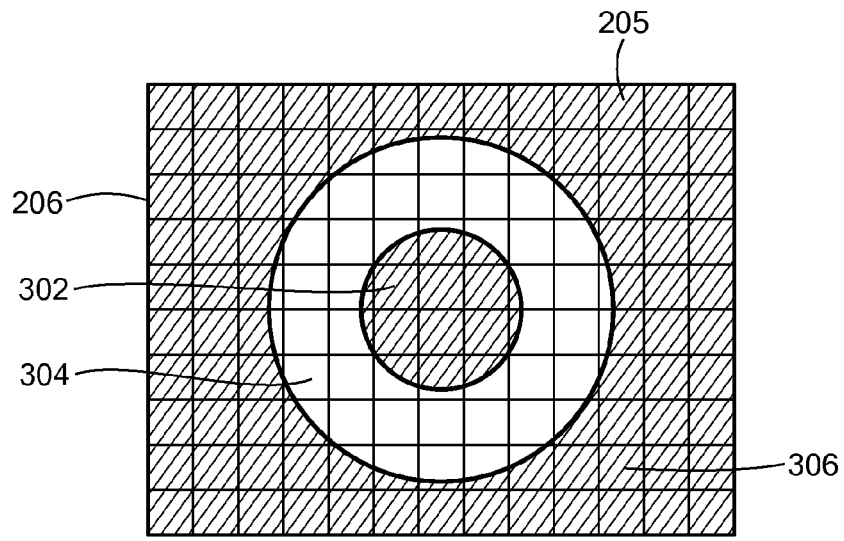
FIGS. 3A and 3B are representations of energy impinging upon an array detector in the system of FIG. 2.

As shown in FIG. 2, and in more detail in FIG. 3A, an image 206 is a conceptualization of the energy appearing on the array detector 204 due to the probe laser beam 108 diverging after having passed through the heated portion of the sample solution 104. The image 206 is a construct for purposes of illustration or explanation and it is not necessary that there be a visible image upon the detector 204. One of ordinary skill in the art can understand that the image 206 could be generated from an output of the detector 204. A central portion 302 of the image 206 represents an area where no (or very little) energy from the probe laser beam 108 falls upon the array detector 204, after having traversed the sample solution 104. As shown, the central portion 302 is surrounded by an annular portion 304 representing the result of the probe laser beam 108 diverging The energy of the probe laser beam 108 appears in the annular "doughnut" region 304. There is no (or very little) detectable energy in either of the "doughnut hole" 302 nor in a region 306 outside the doughnut region 304. When the alignment is near-perfect, the image is sharp. Slight misalignments will cause the doughnut image to lose symmetry about a center or reference point. The center-point of the image represents the intended optical path as oriented with the matrix detector 204.

The image 206 represents a substantially co-linear arrangement of the excitation laser beam 106 and the probe laser beam 108. When the two laser beams are in this dual-opposed configuration, then the probe laser beam 108, i.e., the image 206, will be exhibited as a near symmetric "doughnut" image, as shown in FIG. 3A.

Figure 3B:
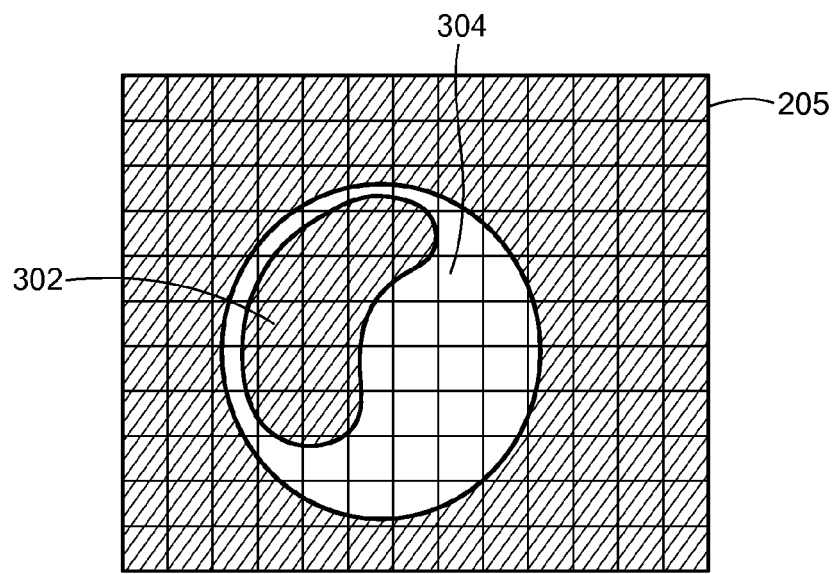

If, however, the excitation laser beam 106 and the probe laser beam 108 are not co-linear, the central portion 302 would not be substantially circular but, rather, would be distorted, e.g., a crescent shape as shown in FIG. 3B. Thus, advantageously, the system 200 provides for a geometric measure (shape), rather than a noisy amplitude measure as to the co-linearity of the excitation laser beam 106 and the probe laser beam 108 along an optical path. Where the array detector 204 indicates that the two laser beams are co-linear, then more accurate measurements of the sample solution 104 can be obtained. Further, a better signal-to-noise ratio is provided as there is no need for the filter 110 as used in conventional systems, i.e., systems with both laser beams directed in the same direction.

In accordance with the embodiment shown in FIGS. 2 and 3A, 3B, the image 206 provides a geometric measure as to alignment as opposed to only measuring amplitude as provided by the diode detector 112 of the known system using the aperture-limited probe laser beam 108 as shown in FIG. 1. The image 206 provides a control variable to measure and maintain alignment of the two laser beams. As is known, misalignment of the two beams is a source of inaccuracy in spectroscopic measurement systems. The relative symmetry of the center portion 302 and the annular surrounding portion 304 is a direct and noise-free measure of the thermal lens effect representing alignment of the two laser beams.

As above, a greater signal-to-noise ratio is obtained due to the elimination of the filter 110 which reduces accuracy in conventional systems. Further, the sensitivity and resolution of the system is enhanced as the appearance of the desired "doughnut" image can be detected immediately upon its occurrence, thus providing a very responsive alignment system and indication.

Figure 4:
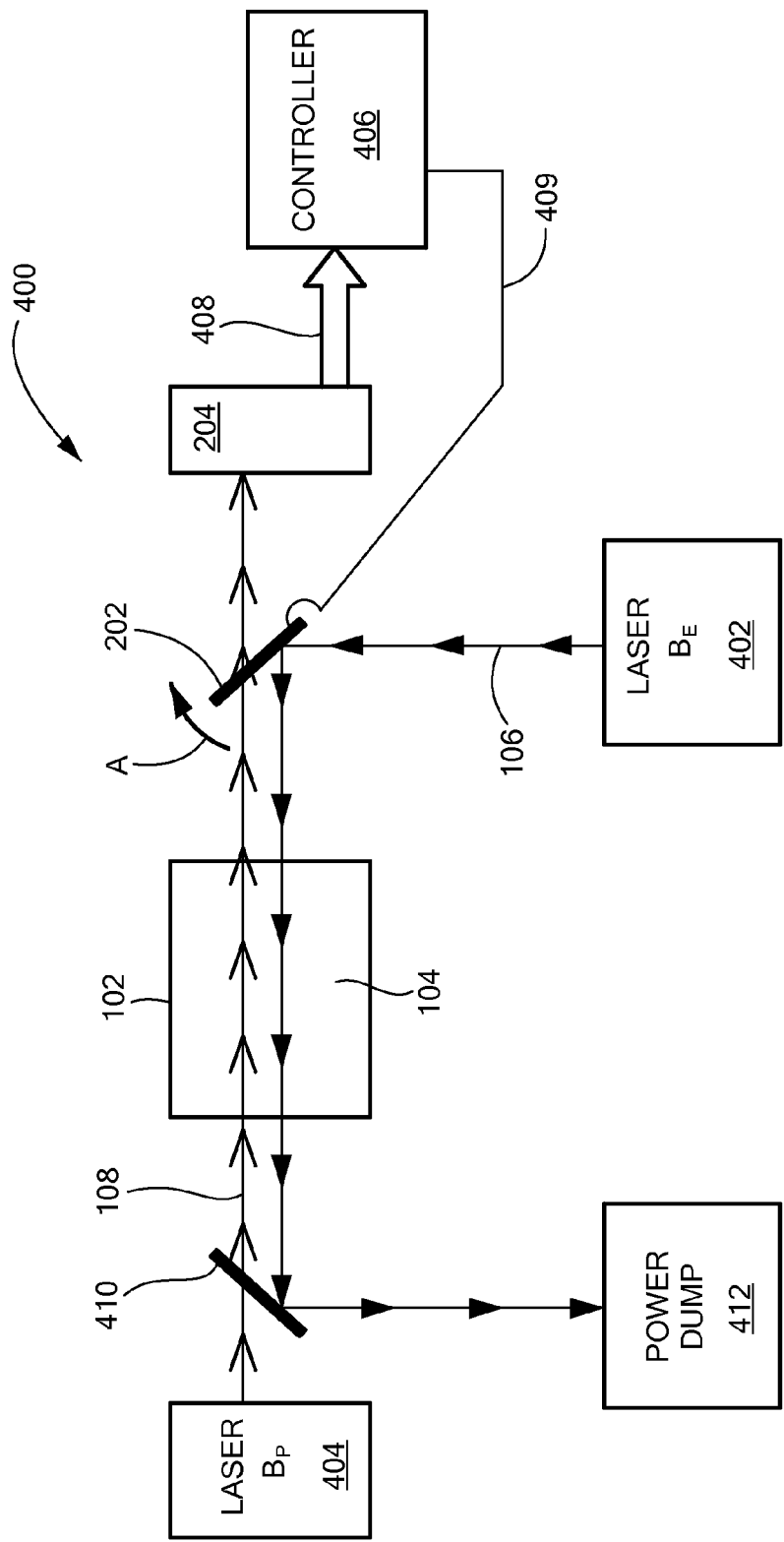
FIG. 4 is a block diagram of a thermal lens spectroscopy system in accordance with another embodiment of the present invention.

In one embodiment of the present invention, the detection of the opposing excitation laser beam 106 and the probe laser beam 108 on the array detector 204 can be used to keep the two laser beams co-linear with one another. A system 400, referring now to FIG. 4, includes an excitation laser beam source 402 and a probe laser beam source 404. The array detector 204 is coupled to a controller 406 via a data link 408 as would be understood by one of ordinary skill in the art. The controller 406 is coupled, via a control line 409, to the beam splitter 202. In addition, a deflection mirror 410 is provided to deflect the excitation laser beam away from the probe laser beam source 404 so as not to damage the device. In one embodiment, the deflected excitation laser beam 106 may be diverted to a power dump 412 as known to those of ordinary skill in the art. The controller 406 is configured to receive the image information from the array detector 204, via the data link 408, and configured to determine if the excitation laser beam 106 and the probe laser beam 108 are co-linear. If it is determined that the two laser beams are not co-linear, the controller 406 will then adjust an angle A of the beam splitter 202 to attain co-linearity. Of course, one of ordinary skill in the art will understand that the system can be configured to also adjust the orientation of the excitation laser beam by implementation of known methods.

The controller 406 may include a processor running appropriate software in accordance with the teachings contained herein. The processor may be a known implementation having a CPU, memory, storage, I/O device, etc., and may be coupled to a display on which a rendering of the image 206 is presented. The software to run the system can be written in any one or more of a number of known programming languages and the components can be connected to one another by any of a number of known interconnecting mechanisms and protocols. Further, the operating system can be Windows, Unix, Linux, Apple OS, etc.

The function of the matrix detector 204 and the controller 406 may be provided in a single controller module where the data link 408 is internal. Still further, the matrix detector 408 could be incorporated onto the same die on which the controller is implemented, providing for a very small package, increased speed, and increased reliability.

Figure 5:
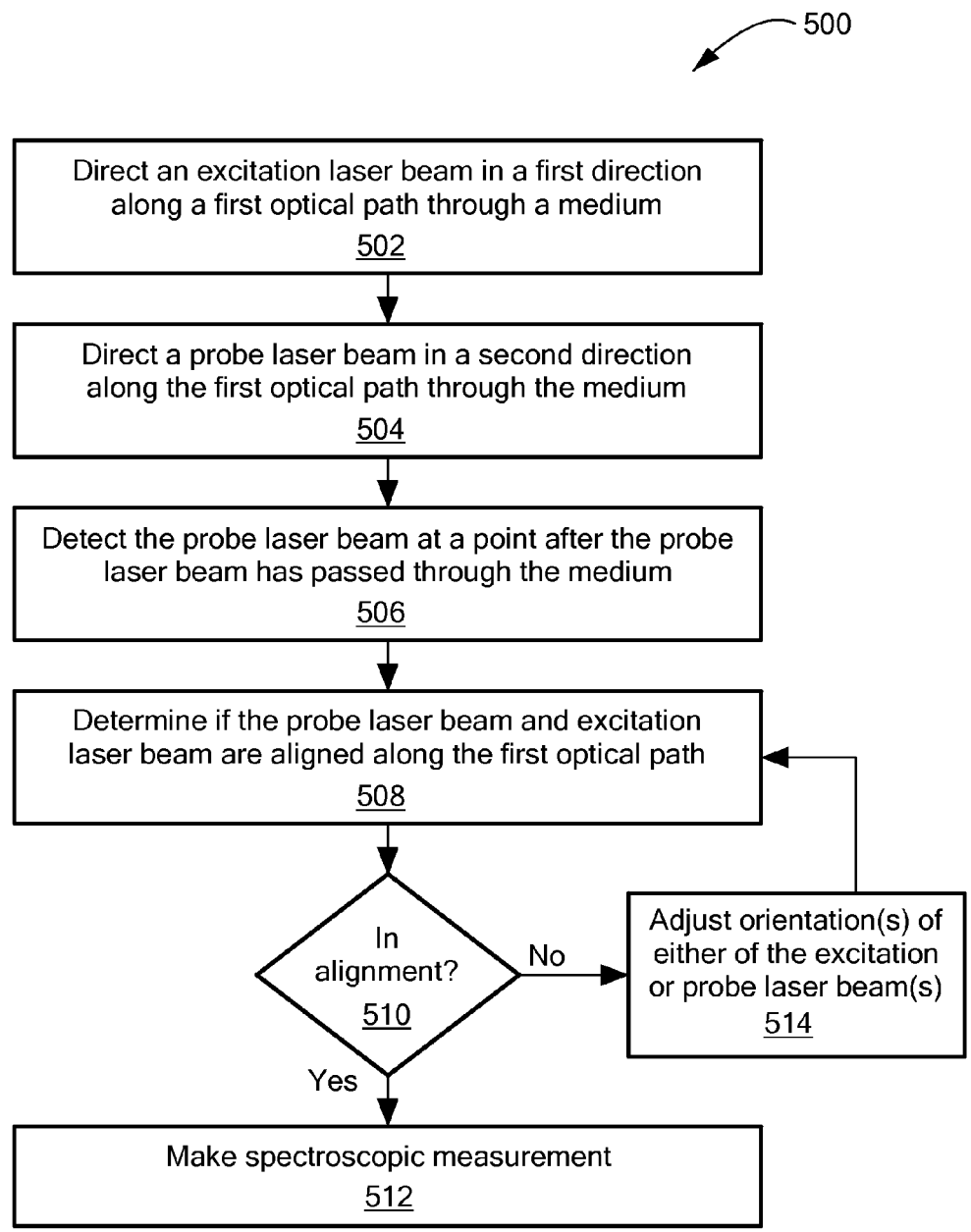
FIG. 5 is a flowchart of a method in accordance with an embodiment of the present invention.

A method 500 of photothermal spectroscopy, in accordance with one embodiment of the present invention is presented in FIG. 5. At step 502, an excitation laser beam is directed in a first direction along a first optical path through a medium. Subsequently, step 504, a probe laser beam is directed in a second direction along the first optical path through the medium, where the second direction is opposite to that of the first direction. The probe laser beam is detected at a point located after the probe laser beam has passed through the medium, step 506. It is then determined if the probe laser beam and the excitation laser beam are coaxially or co-linearly aligned along the first optical path, step 508. At step 510, if it is determined that the two laser beams are in alignment, then control passes to step 512 where a spectroscopic measurement, or the like, can be taken. Returning to step 510, in the event that the two laser beams are not aligned, control passes to step 514 where at least one of an orientation of the excitation laser beam and the probe laser beam is adjusted after which control returns to step 508 to determine if the two laser beams are aligned.

When the alignment of the opposing beams is detected and maintained, as described above, the geometric features of the image can be measured relatively independently of possibly interfering amplitude noise sources. In one embodiment, the radius of the region 304 is an independent measure of the amount of the absorption of the sample. This measure may be more accurate than the amplitude measurement of known systems not using opposed laser beams. Further, any radius variation over time may contain additional information with respect to measurements of the unknown sample.

While the alignment of the two laser beams is being maintained, the amplitude measurement of the integrated doughnut image signal 206 will not be degraded by excitation laser beam amplitude noise.

In another application of an embodiment of the present invention, the ability to accurately align a laser beam can be applied to cavity ring-down spectroscopy. As is known, cavity ring-down spectroscopy is used to measure concentrations of substances that, generally, absorb light.

Figure 6:
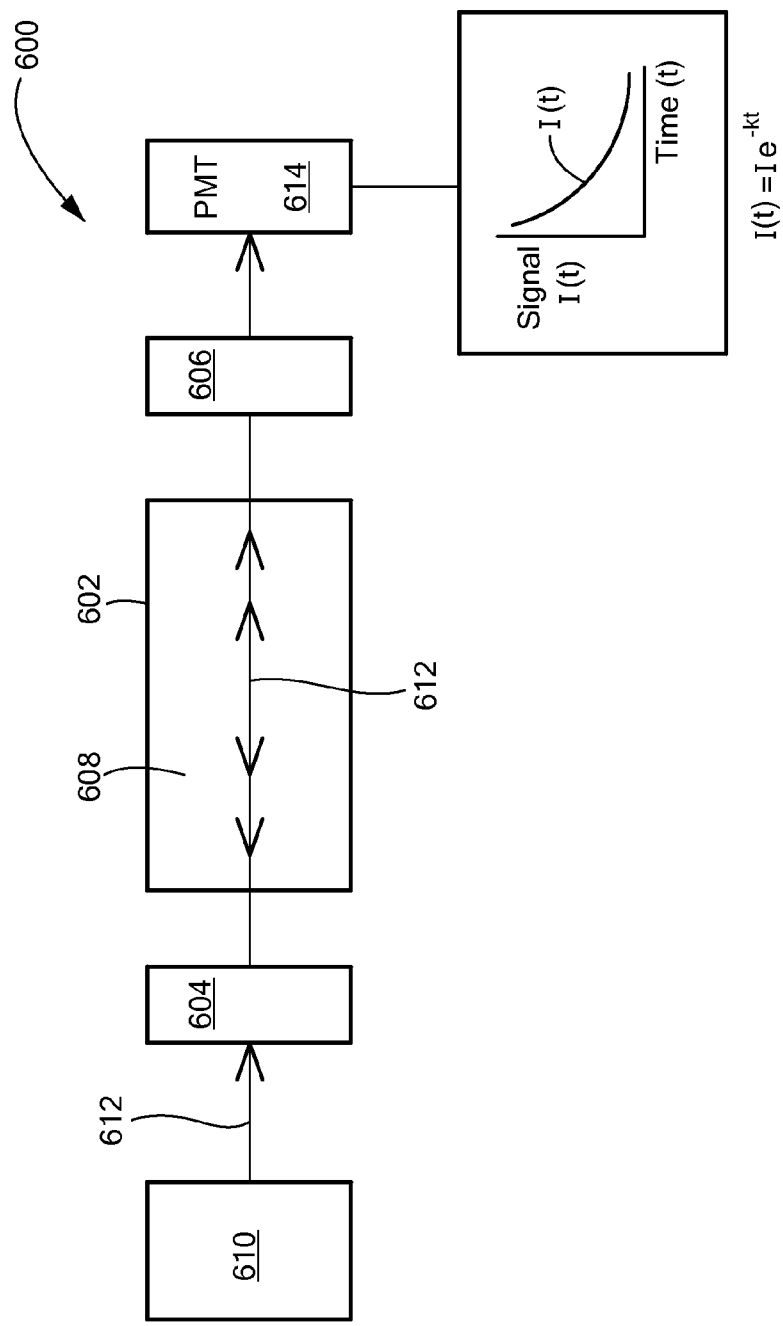
FIG. 6 is a diagram of a known cavity ring-down spectroscopy system.

A known cavity ring-down spectroscopy (CRDS) system 600 is presented in FIG. 6 and its operation is generally understood by one of ordinary skill in the art. As an overview, a cavity 602 is provided between first and second mirrors 604, 606 that are positioned so that their reflective surfaces are facing each other. A light absorbing gas 608 is provided within the cavity 602. A laser 610 provides either a continuous wave (CW) or a pulse, or series of pulses, of laser light 612 into the cavity 602. The laser beam 612 then bounces back and forth between the reflective surfaces of the first and second minors 604, 606.

As is known, a small amount of the laser light 612 may leak out of the cavity 602 and this is measured, e.g., by a photomultiplier tube (PMT) device 614, and it can be measured each time the laser beam hits one of the mirrors. Some amount of light is lost on each reflection and, therefore, the amount of light energy hitting the minors 604, 606 is slightly less each time. Further, because a percentage of the light leaks through, an amount of light measured also decreases at each reflection. If a substance that absorbs light is placed in the cavity 602, for example, the light absorbing gas 608, there will be fewer detections of the light that leaked out before all of the light energy is exhausted.

As is known, the CRDS system measures how long it takes for the light to drop to a certain percentage of its original amount and this "ring-down" time can be converted to a concentration in accordance with the formula $I(t)=Ie^{-kt}$. The CRDS system 600 measures the parameter "k" to determine the amount of contaminants and/or the type of contaminants within the absorbing gas 608. There is, however, no alignment control of the laser beam 612 with respect to the first and second mirrors 604, 606. The system is, therefore, sensitive to laser fluctuations and there is no independent absorption reference.

Figure 7:
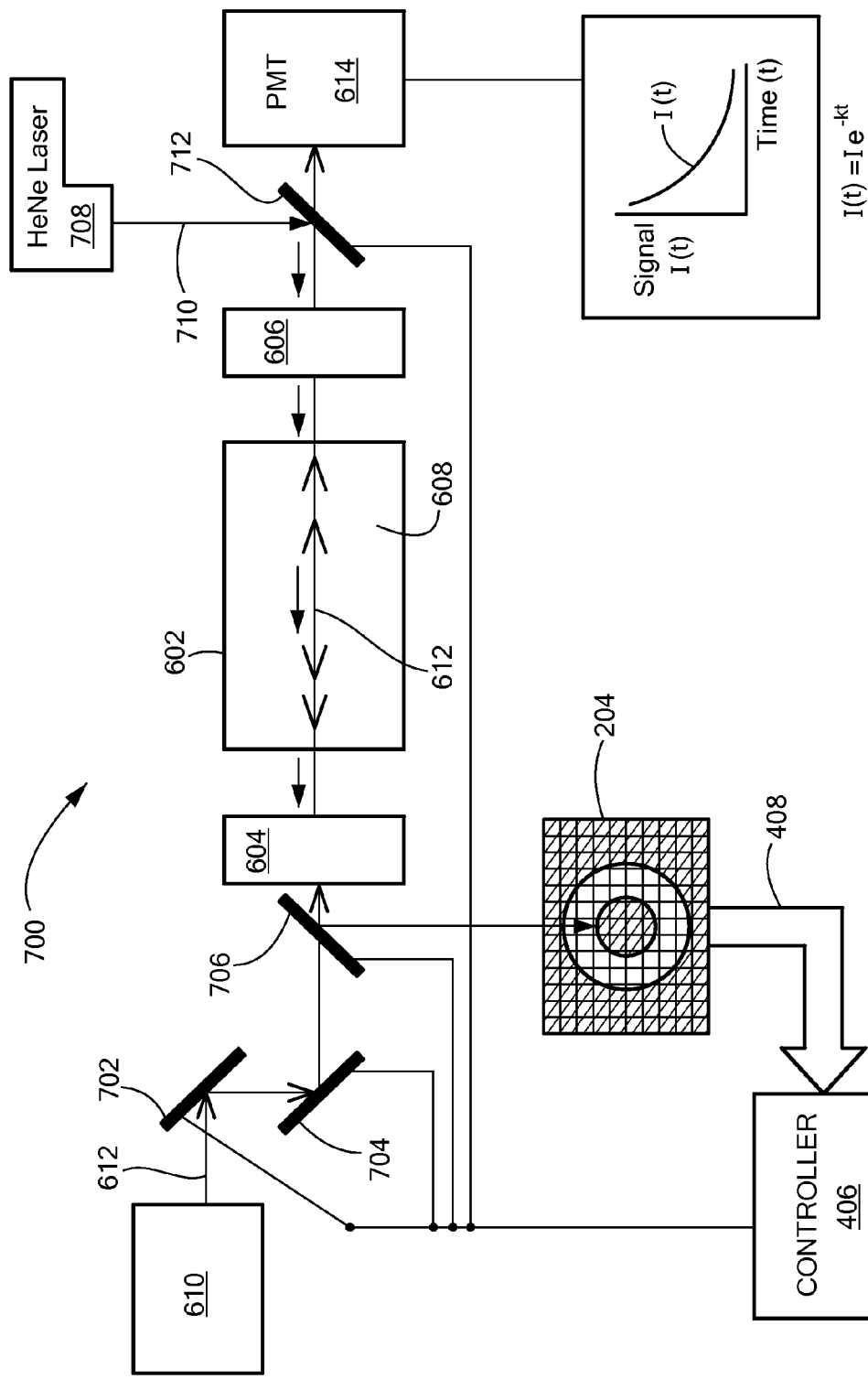
FIG. 7 is a cavity ring-down spectroscopy system in accordance with an embodiment of the present invention.

Referring now to FIG. 7, a cavity ring-down spectroscopy system 700 in accordance with an embodiment of the present invention is presented. Those elements in the system 700 that are the same as those previously described with reference to other figures are similarly identified. In the system 700, the laser device 610 provides the first laser beam 612 via first and second reflecting mirrors 702 and 704 to direct the first laser beam 612 into the cavity 602. A half silvered minor 706, or its equivalent as known to those of ordinary skill in the art, is also positioned. The first laser beam 612 passes through the half silvered mirror 706 on its way into the cavity 602.

A second laser device 708, e.g., a HeNe laser, provides a second laser beam 710 through a half silvered minor 712 in order to direct the second laser beam 710 so as to define the desired optical path, i.e., the second laser beam 710 defines the path along which the first laser beam 612 should be traveling. Similar to that which has been described above, the second laser beam 710 is reflected by the half silvered minor 706 onto the matrix detector 204.

As described above, the controller 406, coupled to the matrix detector 204 via the data path 408 determines alignment as identified by the signal received from the second laser beam 710 passing through the lower density of the absorbing gas 608 as left behind by the excitation energy of the first laser beam 612. The controller is coupled to the minors 702, 704, 706 and 712 in order to adjust their angles so as to better align the laser beam 612 and the second laser beam 710 based on the received signal.

Figure 8:
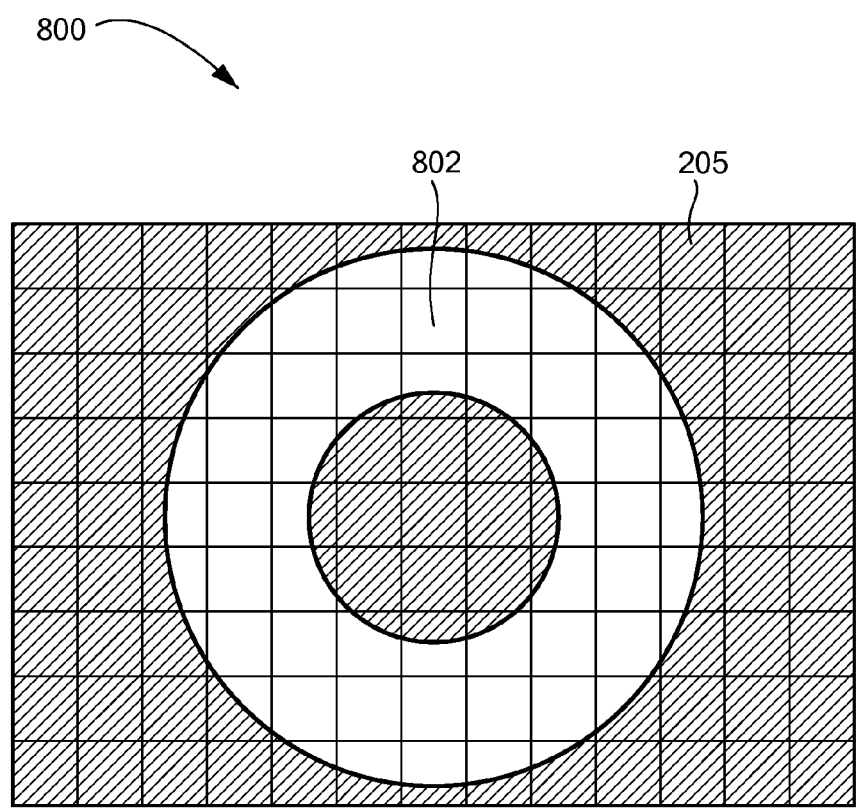
FIG. 8 is a representation of energy impinging upon an array detector in the system of FIG. 7.

Advantageously, in the embodiment of the present invention shown in FIG. 7, an image 800, as shown in FIG. 8, represents alignment of the first laser beam 612 because a first portion 802 of the signal will be shown to be symmetrical, i.e., circular, when the first laser beam 612 is traveling along the desired path defined by the second laser beam 710. A symmetrical "doughnut" image on the matrix detector 204 identifies an aligned system. Further, the image detected by the matrix detector 204 also provides a reference absorption radius measure that can be used to further increase the accuracy of measurements taken by the cavity ring-down spectroscopy system.

A CRDS system using the opposed lasers as described above may alternately determine the orientation of the lasers with the decay-time measurement. In this manner, the second laser beam 710 will not interfere with the measurement. In addition, the second laser beam 710 may be operating at a different wavelength from that of the first laser beam 612. Further, the second laser beam 710 may be pulsed at either a same or different rate as the first laser beam 612 when a pulsed mode of operation is being used. Still further, the system may be "calibrated" for alignment using a standard cavity 602 with a known liquid or gas or a liquid or gas similar to the unknown to be analyzed.

Using the dual opposing laser beam approach, as described herein, to provide alignment for a CRDS system, the probe laser beam doughnut image can be used to improve the "ring-down" amplitude measurement. During the calibration measurement, before the sample is introduced into the cavity, the probe beam doughnut image can be used for alignment. When the sample is introduced, the excitation laser beam focus can be adjusted to provide a negative thermal lens thus causing a probe laser beam doughnut image during the CRDS time constant measurement. A "doughnut ring down time constant," e.g., a change in radius over time, can be measured independently of the excitation signal ring down time constant. This "doughnut ring down time constant" may be used to characterize the unknown sample. Any geometric parameter, e.g., radius, symmetry, etc., and/or any changes thereto, of the probe beam doughnut image 206 on the mosaic array 204 can be used as the measured parameter of the image 206 to provide additional noise-free measurement data.

While embodiments of the present invention have been described with respect to thermal lens spectroscopy and CRDS systems, the present invention is not limited to only these types of spectroscopic systems. These were merely provided as examples of systems where the present invention can be leveraged to provide accurate co-linear positioning of opposing laser beams or additional modes of measurement.

Any system that needs to co-linearly locate two laser beams can be made more accurate by the present invention.

Further, for ease of understanding a "doughnut" image was presented to conceptualize, and therefore aid in the explanation of, the energy falling upon the matrix array detector. It should be understood that capturing an image is only one embodiment of the invention and that there are other embodiments covered by the scope of this disclosure that do not require the generation of an image. In one non-limiting example, the arrangement and number of detectors that detect some threshold level of energy may be analyzed to determine symmetry, asymmetry, etc., without generating an image. Still further, as the image is a construct or aid for explanatory purposes, embodiments of the present invention include those where no image is generated or presented.

The analysis of the doughnut image or distribution may incorporate the application of algorithms that quantify the distribution according to mathematical formulae for comparison with levels of alignment. Further, the data detected by the detector may be stored for subsequent analysis or historical record keeping to monitor the accuracy or "drift" of the system.

The configuration of two opposing laser beams through the sample solution provides a capability for improved alignment measurement, amplitude measurement and geometric measurement. The alignment measurement can be controlled and maintained during the spectrometry measurement time interval. The resulting probe beam doughnut image has a relatively noise-free amplitude measurement (no unfiltered excitation laser noise). Measurements of geometric parameters of the probe doughnut image on the mosaic array (radius, symmetry, etc.) provide additional measurement capability for the spectroscopy task.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. An apparatus for spectrometry, the apparatus comprising:
    a first laser source adapted to emit an excitation laser beam in a first direction along a first optical path and into a medium;
    a second laser source adapted to emit a probe laser beam in a second direction along the first optical path and through the medium, the second direction opposite the first direction;
    a detector oriented to detect the probe laser beam after passing through the medium; and
    a controller, coupled to the detector, adapted to maintain co-linearity of the excitation laser beam and the probe laser beam as a function of the detected probe laser beam.

2. The apparatus of claim 1, wherein the detector comprises:
    a matrix array of detectors oriented to receive the probe laser beam.

3. The apparatus of claim 2, wherein the matrix array comprises a plurality of charge-coupled devices (CCDs).

4. The apparatus of claim 3, wherein at least one of the CCDs comprises an Electron Bombarded CMOS device.

5. The apparatus of claim 1, wherein co-linearity of the excitation laser beam with the probe laser beam is a function of a location of the probe laser beam with respect to a first portion of the volume of the medium altered by the excitation laser beam.

6. The apparatus of claim 1, wherein the controller is further adapted to analyze a distribution of the detected probe laser beam about a reference point, and
    wherein co-linearity of the first and second laser beams is directly related to an amount of symmetry of the distribution of the detected energy about the reference point.

7. The apparatus of claim 1, wherein a power level of the excitation laser beam is greater than a power level of the probe laser beam.

8. A method of controlling accuracy of first and second laser beams in a spectrometry system, the method comprising:
    generating a first laser beam in a first direction along a first optical path through a medium;
    generating a second laser beam in a second direction, opposite the first direction, along the first optical path and through the medium;
    detecting energy of the second laser beam after passing through the medium; and
    maintaining co-linearity of the first and second laser beams with one another as a function of the detected energy.

9. The method of claim 8, further comprising:
    generating an image from the detected energy; and
    maintaining co-linearity of the first and second laser beams as a function of the generated image.

10. The method of claim 9, wherein the generated image geometrically represents an amount of co-linearity of the first and second laser beams.

11. The method of claim 9, further comprising:
    determining co-linearity of the first and second laser beams as a function of an amount of symmetry of the generated image about a reference point.

12. The method of claim 8, further comprising:
    providing the first laser beam with a higher energy than the second laser beam.

13. The method of claim 8, further comprising:
    performing a spectrometric analysis of the medium.

14. The method of claim 13, wherein performing the spectrometric analysis comprises:
    performing a cavity ring-down analysis of the medium as a function of a degradation of the first laser beam.

15. The method of claim 14, further comprising:
    performing the cavity ring-down analysis during a time period when the second laser beam is not passing through the medium.

16. The method of claim 8, further comprising:
    analyzing a distribution of the detected energy about a reference point; and
    maintaining co-linearity of the first and second laser beams as a function of the distribution,
    wherein co-linearity of the first and second laser beams is directly related to an amount of symmetry of the distribution of the detected energy about the reference point.

17. The method of claim 16, further comprising:
    analyzing a geometric spread of the detected energy about the reference point.

18. The method of claim 17, further comprising:
    determining one or more characteristics of the medium as a function of the geometric spread of the detected energy.

19. The method of claim 8, further comprising:
    determining one or more geometric parameters of a distribution of the detected energy; and determining one or more characteristics of the medium as a function of the determined geometric parameters.

20. The method of claim 19, further comprising:
determining changes, over time, of the one or more geometric parameters of the detected energy distribution; and
determining one or more characteristics of the medium as a function of the determined changes in the geometric parameters.

21. A method of maintaining co-linearity of first and second laser beams, wherein the second laser beam defines an optical path along which the first laser beam is to be aligned, the method comprising:
generating the first laser beam in a first direction along the optical path through a medium;
generating the second laser beam in a second direction, opposite the first direction, along the optical path and through the medium;
detecting energy of the second laser beam after passing through the medium; and
maintaining the co-linearity of the first and second laser beams with one another as a function of the detected energy,
wherein the first laser beam has a higher energy than the second laser beam.

22. The method of claim 21, further comprising:
analyzing a distribution of the detected energy about a reference point; and
maintaining co-linearity of the first and second laser beams as a function of the distribution,
wherein co-linearity of the first and second laser beams is directly related to an amount of symmetry of the distribution of the detected energy about the reference point.

23. The method of claim 21, further comprising:
determining one or more geometric parameters of a distribution of the detected energy; and
determining one or more characteristics of the medium as a function of the determined geometric parameters.

24. The method of claim 23, further comprising:
determining changes, over time, of the one or more geometric parameters of the detected energy distribution; and
determining one or more characteristics of the medium as a function of the determined changes in the geometric parameters.

25. A method of characterizing a medium, the method comprising:
generating a first laser beam in a first direction along an optical path through the medium;
generating a second laser beam in a second direction, opposite the first direction, along the optical path and through the medium;
detecting energy of the second laser beam after passing through the medium;
maintaining co-linearity of the first and second laser beams with one another as a function of the detected energy; and
determining one or more characteristics of the medium as a function of the detected energy,
wherein the first laser beam has a higher energy than the second laser beam.

26. The method of claim 25, wherein determining one or more characteristics of the medium comprises:
analyzing a distribution of the detected energy about a reference point.

27. The method of claim 26, further comprising:
analyzing a geometric spread of the distribution of the detected energy about the reference point.

28. The method of claim 25, further comprising:
determining one or more geometric parameters of a distribution of the detected energy; and
determining one or more characteristics of the medium as a function of the determined geometric parameters.

29. The method of claim 28, further comprising:
determining changes, over time, of one or more geometric parameters of the detected energy distribution; and
determining one or more characteristics of the medium as a function of the determined changes over time of the one or more geometric parameters.

* * * * *

UNITED STATES PATENT AND TRADEMARK OFFICE
CERTIFICATE OF CORRECTION

| | | |
|---|---|---|
| PATENT NO. | : 7,852,472 B1 | Page 1 of 1 |
| APPLICATION NO. | : 12/174796 | |
| DATED | : December 14, 2010 | |
| INVENTOR(S) | : William M. Johnson | |

It is certified that error appears in the above-identified patent and that said Letters Patent is hereby corrected as shown below:

Column 7, line 39, "minors" should read --mirrors--;

Column 7, line 64, "minor" should read --mirror--;

Column 8, line 2, "minor" should read --mirror--;

Column 8, line 7, "minor" should read --mirror--; and

Column 8, line 14, "minors" should read --mirrors--.

Signed and Sealed this
Twenty-ninth Day of May, 2012

David J. Kappos
*Director of the United States Patent and Trademark Office*